United States Patent [19]
Fukaya et al.

[11] Patent Number: 5,552,929
[45] Date of Patent: Sep. 3, 1996

[54] STEREOMICROSCOPE

[75] Inventors: Takashi Fukaya, Hachiouji; Masami Hamada, Akishima; Shinichi Nakamura, Hachiouji; Toyoharu Hanzawa, Fuchu; Masahiko Kinukawa, Hachiouji; Tomonori Ishikawa, Hachiouji; Hiroshi Fujiwara, Hachiouji; Shigeo Tokunaga, Hino, all of Japan

[73] Assignee: Olympus Optical Co., Ltd., Tokyo-to, Japan

[21] Appl. No.: 411,929

[22] Filed: Mar. 28, 1995

Related U.S. Application Data

[63] Continuation of Ser. No. 203,680, Feb. 28, 1994, abandoned, which is a continuation of Ser. No. 869,172, Apr. 16, 1992, abandoned.

[30] Foreign Application Priority Data

| Jul. 23, 1991 | [JP] | Japan | 3-182319 |
| Oct. 31, 1991 | [JP] | Japan | 3-286562 |
| Nov. 20, 1991 | [JP] | Japan | 3-304933 |
| Dec. 12, 1991 | [JP] | Japan | 3-328779 |

[51] Int. Cl.$^6$ ............ G02B 21/22; G02B 21/00
[52] U.S. Cl. ............ 359/380; 359/368; 359/378
[58] Field of Search ............ 359/368, 369, 359/372–380, 432, 362–363, 385–390

[56] References Cited

U.S. PATENT DOCUMENTS

| 4,138,191 | 2/1979 | Peyman et al. | 359/377 |
| 4,167,302 | 9/1979 | Karasawa | 359/377 |
| 4,341,435 | 7/1982 | Lamp et al. | 359/376 |
| 4,448,498 | 5/1984 | Muller et al. | 359/363 |
| 4,576,450 | 3/1986 | Westphal | 359/372 |
| 4,594,608 | 6/1986 | Hatae et al. | 359/377 |
| 4,605,287 | 8/1986 | Lang | 359/385 |
| 4,657,356 | 4/1987 | Matsumura | 359/385 |
| 4,723,842 | 2/1988 | Twisselmann et al. | 359/380 |
| 4,744,642 | 5/1988 | Yoshinaga et al. | 359/389 |
| 4,763,968 | 8/1988 | Minami et al. | 359/377 |
| 4,798,451 | 1/1989 | Fujiwara | 359/375 |
| 4,802,749 | 2/1989 | Togino et al. | 359/377 |
| 4,871,245 | 10/1989 | Ishikawa et al. | 359/363 |
| 5,052,789 | 10/1991 | Kleinberg | 359/377 |
| 5,132,837 | 7/1992 | Kilajima | 359/374 |

FOREIGN PATENT DOCUMENTS

| 0310514 | 4/1989 | European Pat. Off. |  |
| 1846379 | 3/1961 | Germany . |  |
| 3333471 | 4/1985 | Germany . |  |
| 352639 | 4/1991 | Germany . |  |
| 158410 | 6/1989 | Japan | 359/368 |

*Primary Examiner*—Thong Nguyen
*Attorney, Agent, or Firm*—Cushman, Darby & Cushman

[57] ABSTRACT

A stereomicroscope includes an objective optical system, a variable magnification optical system, and a plurality of imaging optical systems, in which the plurality of imaging optical systems can be moved in a plane perpendicular to the optical axis of the variable magnification optical system. Thus, the stereomicroscope has the advantage that where one of two observers wishes to observe a brighter image, the amount of light can be adjusted, without replacement of a light source, by moving the imaging optical systems.

7 Claims, 17 Drawing Sheets

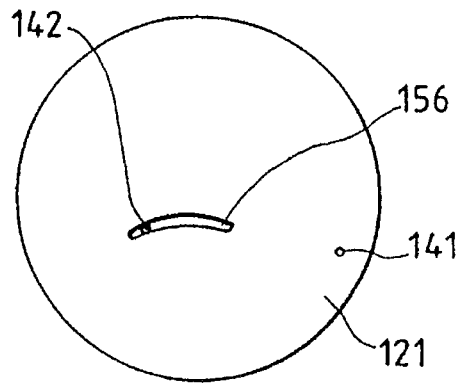
FIG. 10
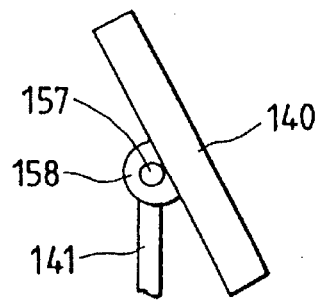
FIG. 11
FIG. 12
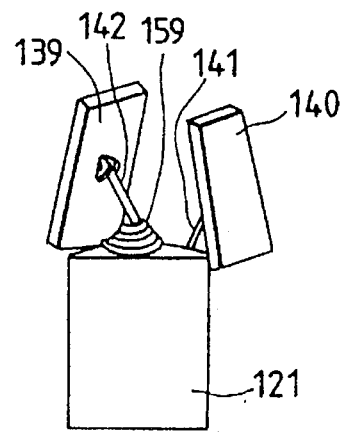
FIG. 13
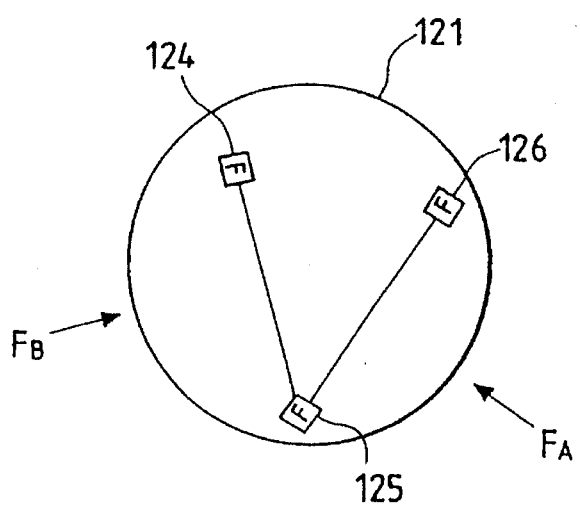

STEREOMICROSCOPE

This is a continuation of application Ser. No. 08/203,680, filed on Feb. 28, 1994, which was abandoned upon the filing hereof which was a continuation of application Ser. No. 07/869,172 filed Apr. 16, 1992 abandoned.

BACKGROUND OF THE INVENTION

1. Field of the Invention

This invention relates to a stereomicroscope for use in surgical operation and the like that a plurality of observers views an object at once.

2. Description of the Prior Art

Recently, for the purposes of education and so on, stereoscopic microscopes have been largely used through which a plurality of persons can observe an object at the same time and with nearly the same magnification.

As one of methods to realize it, there is a observation through a stereoscopic TV. As an example, it has been proposed by Japanese Patent Preliminary Publication No. Hei 1-319721. This example, as depicted in FIG. 1, is designed so that for the stereoscopic view of the stereomicroscope, a pair of imaging optical systems are divided into two optical systems to mount TV cameras at their imaging position, images obtained from the TV cameras on both sides are alternately reproduced on a monitor by a switcher, and the image of the right optical system is observed with the right eye, while that of the left optical system with the left eye. Specifically, light from an object O, after passing through an objective lens 22 and individual variable magnification optical systems 23L and 23R on both sides, is split by beam splitters 24L and 24R so that one of the split light travels in straight lines, traverses imaging lenses 25L and 25R, and is observed as magnified images at eyepieces 26L and 26R, while the other is laterally reflected 90°, passes through imaging lenses 27L and 27R, is further reflected 90° upward from planar mirrors 28L and 28R, and imaged on imaging surfaces 29L and 29R of TV cameras 30L and 30R. The images transmitted from the TV cameras 30L and 30R are alternately displayed on a monitor 32 by a switcher 31. By a scope 33 having shutters 33L and 33R opened and closed in synchronization with the switcher 31, the images of the right and left optical systems are alternately observed with the right and left eyes for the stereoscopic vision.

Japanese Patent Preliminary Publication No. Sho 63-143519 shows the arrangement that, without using any image sensory two sets of first and second stereoscopic observation optical systems and an illumination system for illuminating an object to be detected are disposed behind an objective lens used in common, in which an optical axis deflecting means for the second stereoscopic observation optical system is provided in the vicinity of the pair to the first stereoscopic observation optical system and optically combined with the second stereoscopic observation optical system.

The Hei 1-319721 prior art, however, has developed the defect that a second observer, who does auxiliary work while viewing the picture image of a stereoscopic TV, is hard of work because the stereoscopic TV displays an image viewed from a first observers's observation point. Moreover, the work they must do while viewing the picture image makes their postures unusual and causes difficulty in operation for a long time. In the sho 63-143519 prior art, to prevent mutual interference between two sets of observation optical systems incorporated in the microscope body, oversizing of the microscope body is caused, with resultant inconvenience to operation.

Where the work done making use of the stereomicroscope is complicated and needs accuracy, it is often desired that a plurality of operators does the work in cooperation with one another. Particularly when the steromicroscope is a surgical microscope, under observation through which a surgical operation is to be performed as a cooperative work by a first observer who principally performs the operation and a second observer who aids the operation the two observers should observe an object O in the same situation as far as possible. In other words, it is required that they can obtain the same visual field for observations with the same magnification for observations.

Further, some surgical technique would require that the observers change their relative positions with respect to the object O (in other words, observers' observation directions) during the operation; microscopes meeting such requirement are awaited.

In the past, the stereomicroscope realizing the demands mentioned above has been set forth in Japanese Patent Preliminary Publication No Sho 47-41473, for instance. Referring to FIGS. 2A and 2B, FIG. 2A is a front sectional view and FIG. 2B is a side view. In this stereomicroscope, a pair of variable magnification optical systems 42 is disposed behind a single objective lens 41 located above an object O, and a beam of light passing through the variable magnification optical systems 42 is divided by an optical path splitting member 43 and introduced into a pair of observation optical systems 44 disposed on opposite sides. Two observers can thus observe stereoscopically the object O of the same situation, facing toward each other.

As another measure, the stereomicroscope shown in FIGS. 3A, 3B and 3C is set forth in Japanese Utility Model Publication No. 55-39364. This arrangement is such that at least three sets of variable magnification optical systems 45 located behind the objective lens 41, namely in the figures, two pairs of variable magnification optical systems 45 are disposed to intersect at an angle of 90° with each other and introduces light into two observation optical systems 44. Hence, the first and second observers can observe the object O in the same situation, even from the directions making right angle with each other.

As still another measure, the stereomicroscope depicted in FIG. 4 is stated in Japanese Patent Preliminary Publication No. Hei 2-143215. In this stereomicroscope, an optical path splitting means 48 is disposed in the optical path between a single objective lens 46 and a pair of variable magnification optical systems 47, and another pair of variable magnification optical systems 49 is disposed in the optical path of a part of the light beam split by the optical path splitting means 48 so that two observers can view stereoscopically the object O through the observation optical systems 44. Furthermore, by rotating the optical system including the variable magnification optical systems 49, the angle defined between the two observers' observation directions can be arbitrarily set.

The arrangement of the stereomicroscope shown in FIG. 2A, however, has a drawback that the angle between the two observers' observation directions is limited to 180° cannot be set at any other angle.

For the arrangement in FIGS. 3A, 3B and 3C, the number of the variable magnification optical systems 45 is so large that numerous lenses must be moved when magnification is changed. Accordingly, a mechanism for changing magnification gets complicated, which raises problems such as difficulty of adjustment and increase in size, weight and cost of the microscope there is also the problem that the angle defined by the positions of the two observers is limited to 90°.

As for the arrangement in FIG. 4, although the positions of the two observers can be arbitrarily changed, another pair of variable magnification optical systems must be provided on the optical system of the reflected beam, which fact has the defect that the microscope is brought to oversizing, an increase of weight, and high cost. Further, to put two images to be observed in identical magnification, an interlocking mechanism is required for associating individual variable magnification optical systems with each other, on the condition that the position of the second observer can be altered with respect to the position of the first observer. This has the defects that the arrangement is complicated and the cost is raised.

SUMMARY OF THE INVENTION

It is, therefore, an object of the present invention is to provide a stereomicroscope having a relatively simple arrangement in which a plurality of observers can change their observation directions, while the observers obtain the same images with each other, with respect to axis, magnification and stereoscopic visibility.

According to an aspect of the present invention, the stereomicroscope is designed so that an objective optical system including a variable magnification optical system is incorporated in a microscope body, and two relay optical systems and eyepiece optical systems set for stereoscopic vision are incorporated in a binocular eyepiece barrel, which is disposed to be rotatable with respect to the microscope body, wherein the objective optical system is constructed as a single optical system and the binocular eyepiece barrel can be rotated about the optical axis of the objective optical system. Light emanating from an object point is formed, through the objective optical system, at the relay optical systems as images, which are observed stereoscopically through the eyepiece optical systems. If the binocular eyepiece barrel is properly rotated in relation to the microscope body for changing the observation direction, the images can be observed without being eclipsed in spite that the relay optical systems and the eyepiece optical systems are moved, for the diameter of the exit light from the objective optical system as a single optical system is large enough. Thus, if a plurality of binocular eyepiece barrels are disposed, individual observers can view images under the same conditions.

These and other objects as well as the features and advantages of the present invention will become apparent from the following detailed description of the preferred embodiments when taken in conjunction with the accompanying drawings.

BRIEF DESCRIPTION OF THE DRAWINGS

FIGS. 7 to 18 are views showing the structure, electrical composition, and optical arrangement of a second embodiment;

DETAILED DESCRIPTION OF THE PREFERRED EMBODIMENTS

Figure 1:
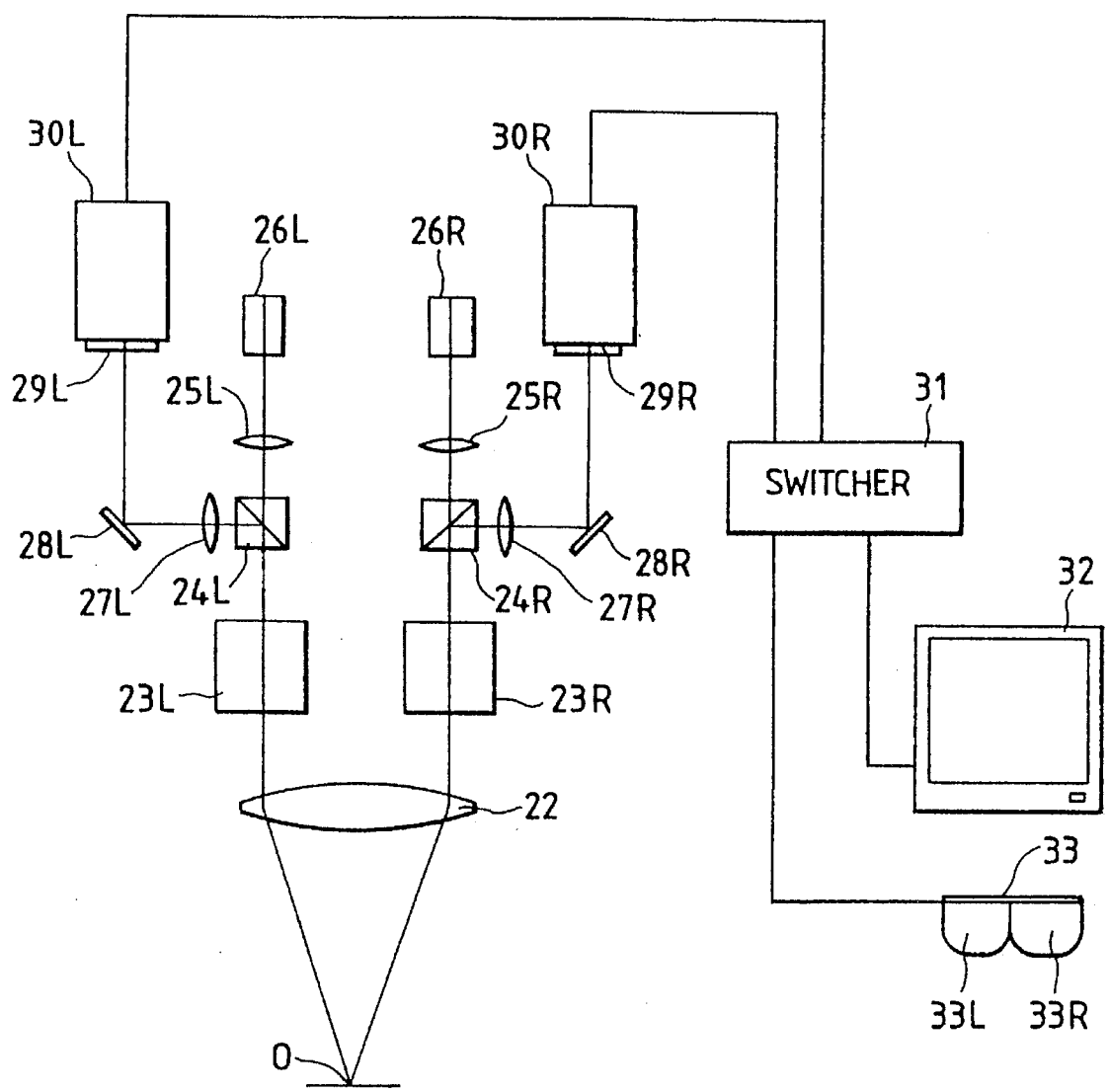
FIGS. 1 to 4 are views showing optical systems of stereomicroscopes according to the prior art.
Figure 2A:
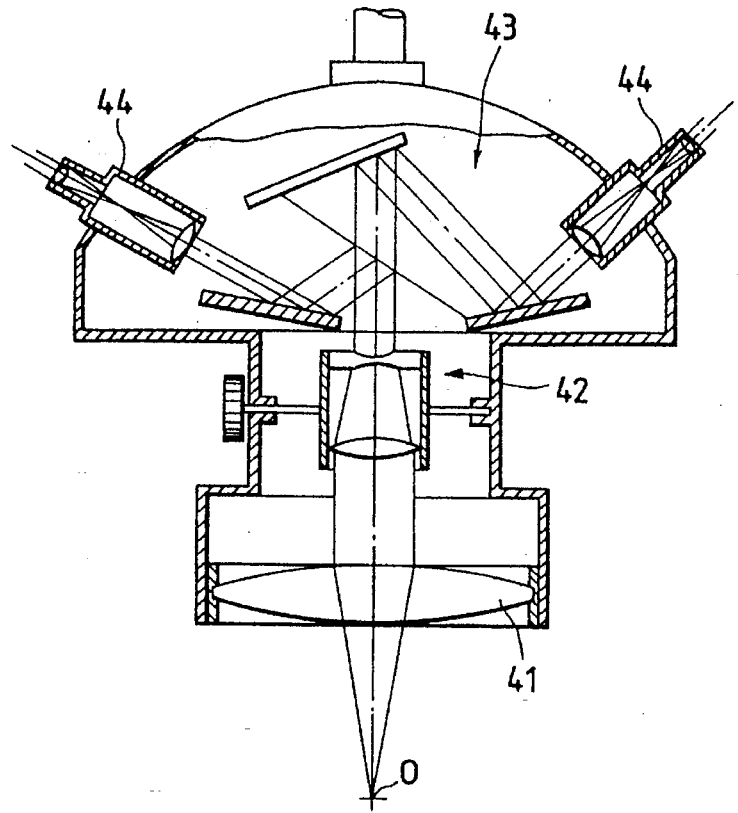
Figure 2B:
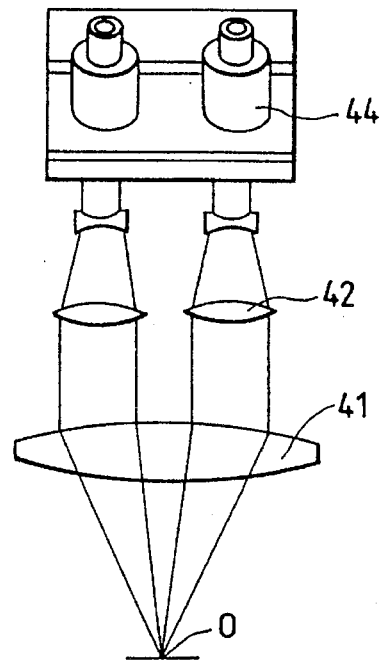
Figure 3A:
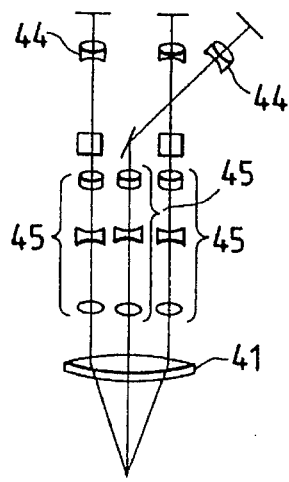
Figure 3B:
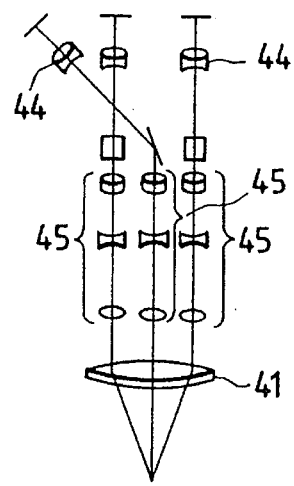
Figure 3C:
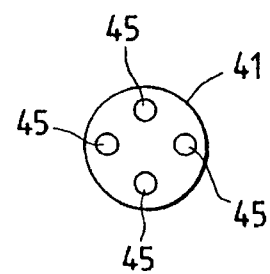
Figure 4:
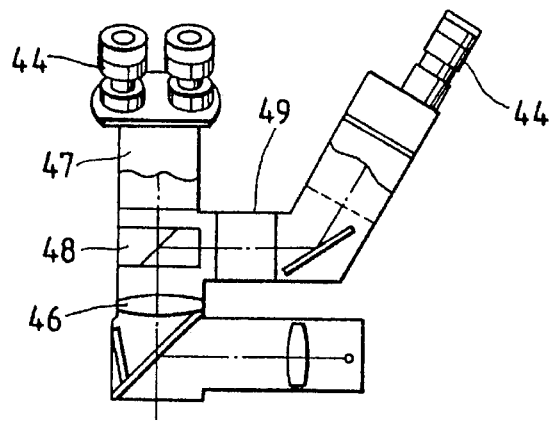

In accordance with the embodiments shown in the drawings, the present invention will be described in detail below.

Figure 5A:
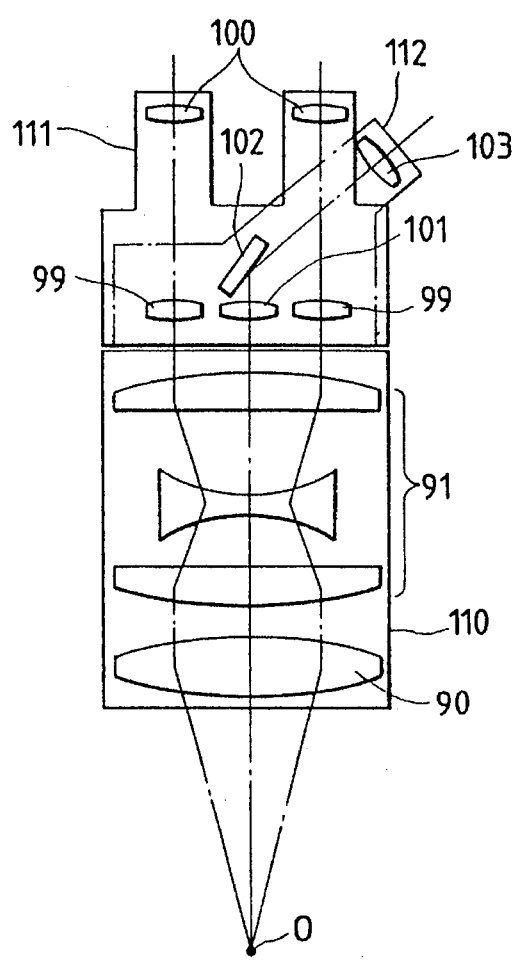
FIGS. 5A, 5B and 6 are views showing the optical system of a first embodiment.
Figure 5B:
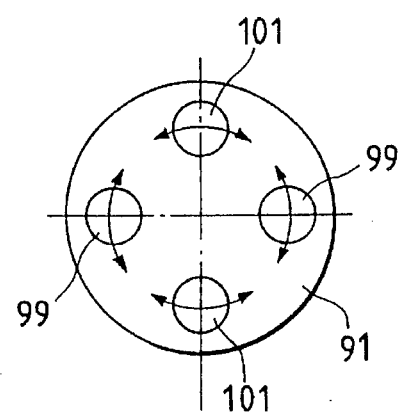

Referring to FIGS. 5A and 5B, a description is given of the first embodiment of the present invention. FIG. 5A is an explanatory view showing the optical system of the stereomicroscope and FIG. 5B is a view showing the positional relationship between the variable magnification optical system and the imaging lenses, looking from the direction normal to FIG. 5A, in which observation optical systems for first and second observers is provided for stereoscopic vision.

In these figures, reference numeral 90 represents an objective lens and 91 a variable magnification optical system. Reference numeral 99 designates a pair of first imaging lenses (a relay optical system) through which the first observer views stereoscopically the object O and 100 a pair of first eyepieces for the first observer, which constitute a first observation optical system. Numeral 101 designates a pair of second imaging lenses (a relay optical system) through which the second observer views stereoscopically the object O; 102 a reflecting mirror for bending the optical paths of imaging beams passing through the second imaging lenses 101; and 103 a pair of second eyepieces positioned on the optical paths, which constitute a second observation optical system. The first and second observation optical systems each includes an image erecting optical system not shown. The objective lens 90 and the variable magnification optical system 91 are incorporated in a microscope body 110, the first observation optical system in a first binocular eyepiece barrel 111, and the second observation optical system in a second binocular eyepiece barrel 112. The first and second binocular eyepiece barrels 111 and 112 are disposed to be capable of rotating, independent of each other, around the optical axis of the variable magnification optical system as for the microscope body 110.

Thus, in the first embodiment, the first and second observers can accomplish the stereoscopic vision of the object O through the first and second binocular eyepiece barrels, respectively. Since the first and second imaging lenses 99 and 101 can be rotated independent of each other in directions indicated by arrows as shown in FIG. 5B by rotating the first and second binocular eyepiece barrels 111 and 112 properly, the observers can make stereoscopic observation while changing their observation directions.

According to the foregoing embodiment, two observers can change their observation directions, and moreover, they can view the object O, with the same axis, magnification, and stereoscopic visibility, and since a light splitting means, such as a half mirror, is not provided between the variable magnification optical system 91 and the two observation optical systems, brighter images can be formed. Additionally, for the first embodiment, if the distances from the object O to the first and second eyepieces 100 and 103 are made equal, the first and second observers can make observations under exactly the same condition. The binocular eyepiece barrels are not necessarily limited to two binocular eyepiece barrels and it is needless to say that three or more binocular eyepiece barrels may be disposed.

Figure 6:
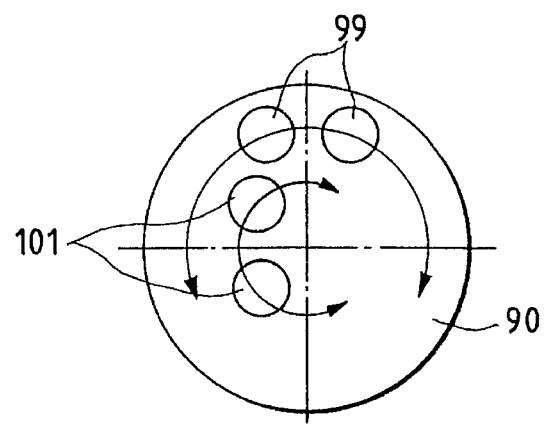

FIG. 6 shows the modification of the first embodiment, in which the first eyepieces 100 of the first binocular eyepiece barrel and the second eyepieces 103 of the second binocular eyepiece barrel are radially shifted from the optical axis of the variable magnification optical system, and the first and second binocular eyepiece barrels are disposed at positions where the eyepieces 100 and 103 and other optical elements can be rotated without any mutual interference.

According to the modification, two observers, although incapable of making observations with exactly the same axis due to the radial shift of the imaging lenses 99 and 101, can do with substantially the same axis because the beams passing through the objective optical system used in common are to be imaged and observed. Moreover, since the first and second imaging lenses 99 and 101 do not interfere with each other, the angle defined between the observers' observation directions can be changed in a wider range.

Figure 7:
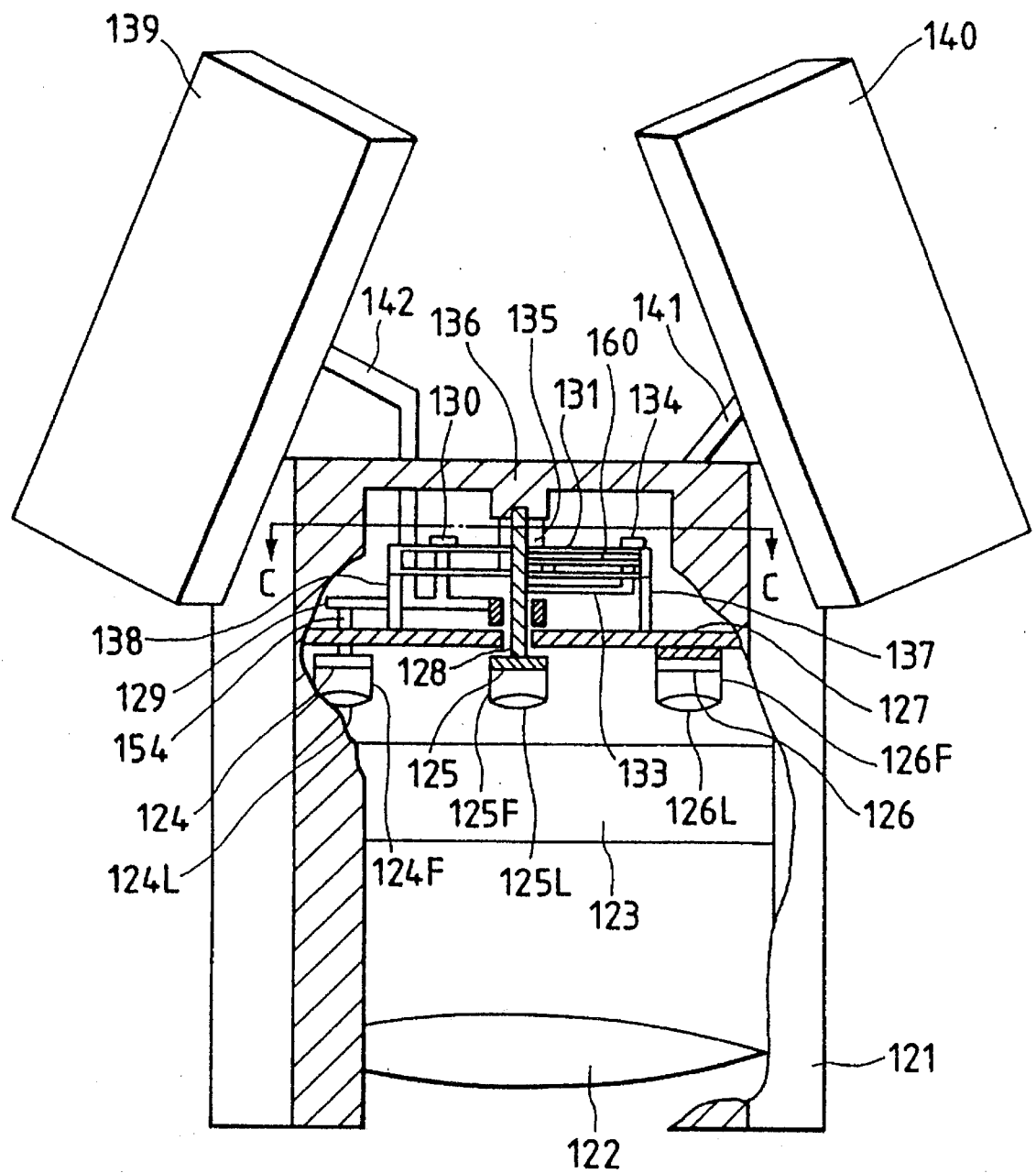

FIGS. 7 to 18 show the second embodiment of the present invention. In FIG. 7 which is a sectional view showing its structure, reference numeral 121 denotes a microscope body, 122 an objective lens disposed at the lower position of the microscope body 121, and 123 a variable magnification optical system disposed above the objective lens 122, for changing observation magnification. Reference numerals 124, 125 and 126 represent image sensors located above the variable magnification optical system 123, which are constructed integral with imaging lenses (relay optical systems) 124L, 125L and 126L and with lens frames 124F, 125F and 126F, respectively. Numeral 127 represents a guide plate secured to the microscope body 121 directly above the image sensors 124, 125 and 126, for supporting the image sensor 126, and 131 an arcuate slit guide fixed to the guide plate 127 by two supporters 137 and 138. Numeral 136 designates a bearing provided on the ceiling of the microscope body 121, and 128 a shaft holding the image sensor 125, rotatably attached to the bearing 136.

Figure 8:
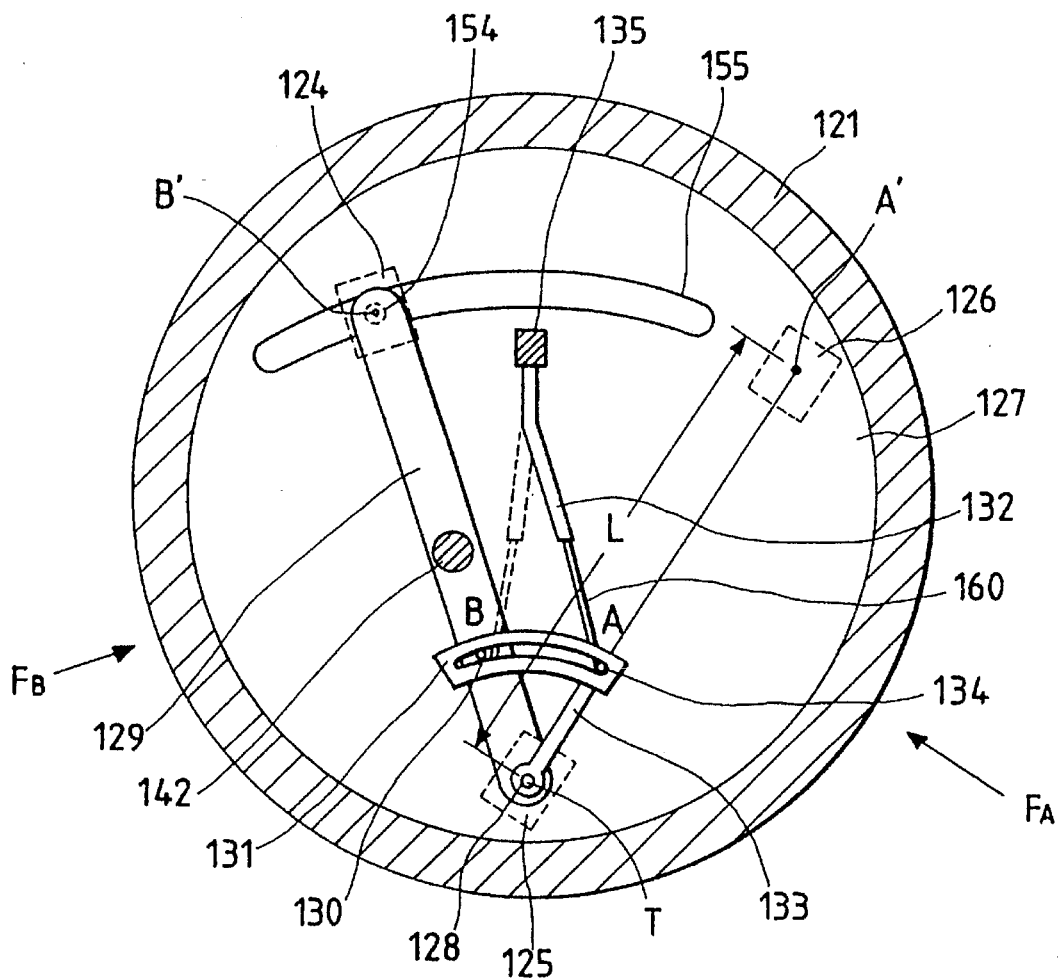

FIG. 8 is a sectional view taken along line C—C in FIG. 7. Reference numeral 133 denotes an arm secured to the shaft 128, with its center at a point T, and 134 a pin plugged into the end of the arm 133, moving along the guide 131. The image sensor 126 is fixed to the guide plate 127 in parallel with the arm 133, with its center at a point A' of a distance L from the point T on the extension of the arm 133. Numeral 132 denotes a bar-shaped piezoelectric element such as a bimorph cell, and 135 a fixed member fixing the piezoelectric element 132 to the microscope body 121. Numeral 160 a driving bar whose one end is attached to the tip of the piezoelectric element 132 and the other engages with the pin 134; 129 a moving arm rotatably attached to the shaft 128, with the point T as the center, through bearings; 154 a moving shaft plugged perpendicularly, with its center at a point B' of the distance L from the point T, into the lower surface of the moving arm 129; and 155 an arcuate guide slit provided in the guide plate 127, for inserting and guiding the moving shaft 154. The image sensor 124 is secured at the lower end of the moving shaft 154. In this case, the image sensor 124 is parallel with the moving arm 129 (T-B'). Also, numeral 130 represents a stopper plugged into the upper surface of the moving arm 129, moving along the guide 131, in which a point A indicates the position where the pin 134 is brought to the right end of the guide 131.

Figure 9:
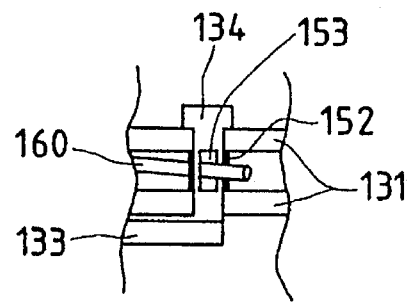

FIG. 9 is a detailed view showing the structure of the pin 134 plugged into the arm 133 and the driving bar 160. Reference numeral 152 designates a damper fixed to the side of the pin 134, and 153 a slit bored through the pin 134, loosely engaging with the other end of the driving bar 160. The damper 152 uses a rubber material to moderate a shock caused by the movement of the pin 134.

FIG. 10 is an upper plan view of the microscope body 121. Reference numeral 156 represents a silt bored in the upper portion of the microscope body 121, and 142 a stand secured at the middle of the upper surface of the moving arm 129, movable along the slit 156 (refer to FIGS. 7 and 8), the stand 142 passing through the upper portion of the microscope body 121 and reaching the outside.

Returning to FIG. 7, reference numeral 139 denotes a monitor (display means) for a first observer held by the stand 142, and 140 denotes a monitor (display means) for a second observer held by the microscope body 121 through a stand 141. The monitor 139 is parallel with the moving arm 129 and the monitor 140 with line A—A'.

FIG. 11 is a detailed view relative to the connection between the monitor 140 and the stand 141. The rear side of the monitor 140 is provided with a retaining portion 158, which is connected to a shaft 157 provided at the end of the stand 141 to be capable of changing the inclination of the monitor 140. The monitor 139 is likewise connected to the stand 142.

FIG. 12 is a view showing the mounting of a cap 159 for preventing dust from entering the microscope on the upper portion of the microscope body 121. The cap 159, made of rubber, is of an expansion bellows type, has two holes through which the stands 141 and 142 pass, and is shaped to fit the upper portion of the microscope body 121.

FIG. 13 is a view showing the directions for mounting the image sensors 124, 125 and 126 when the pin 134 of the arm 133 is positioned at the right end (point A) of the slit 131 in FIG. 8. The image sensors 125 and 126 are mounted in parallel with the arm 133 and the image sensor 124 in parallel with the moving arm 129. Since the image sensors 125 and 126 receive the picture images from the direction of an arrow $F_A$ and the image sensor 124 from the direction of an arrow $F_B$, the image sensor 124 is mounted in the direction opposite to the image sensors 125 and 126.

Figure 14:
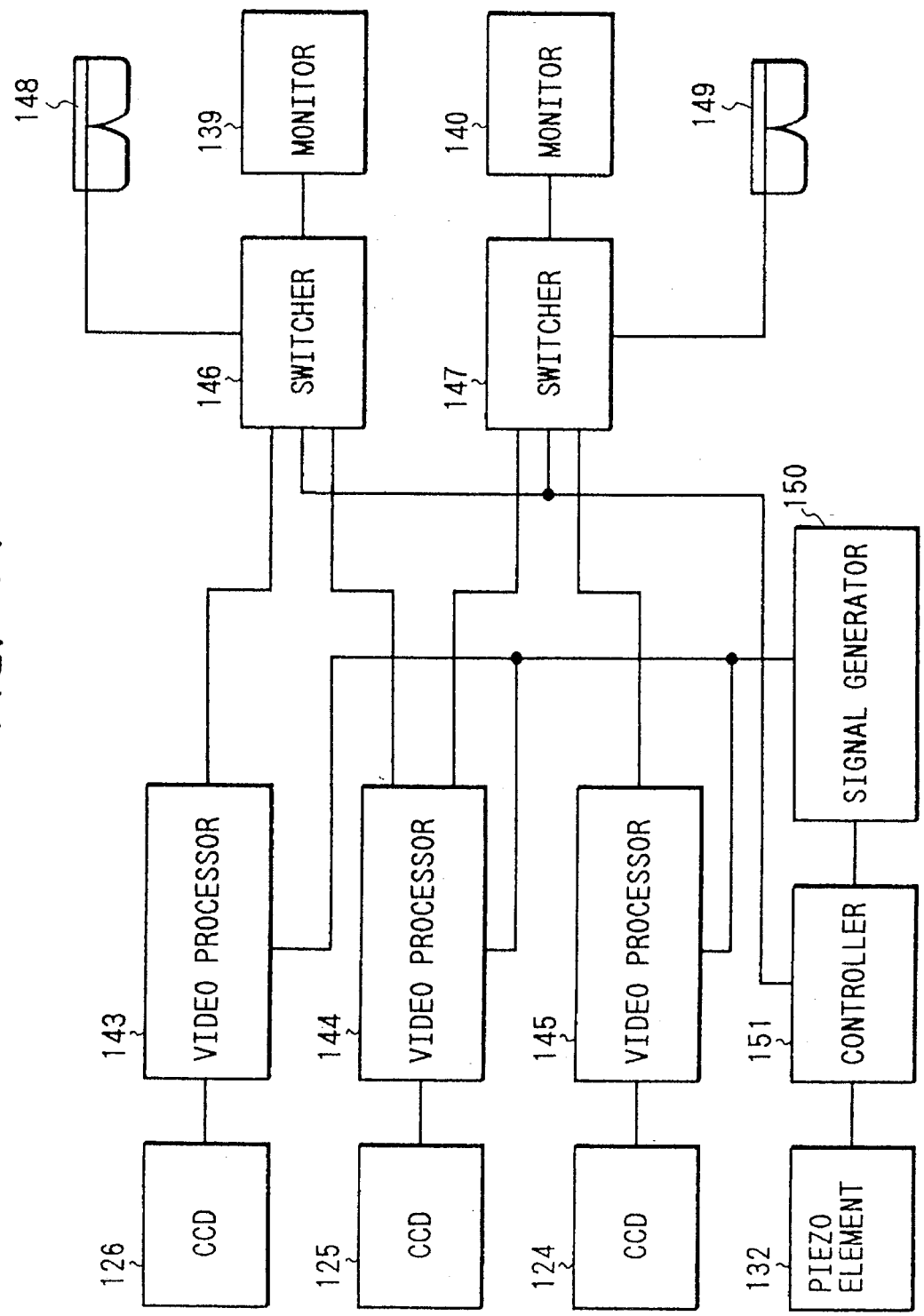

FIG. 14 is a block diagram showing the electrical connection of the second embodiment. Reference numerals 143, 144 and 145 denote video processors; 146 a switcher for compounding the signals of the video processors 143 and 142; 147 a switcher for compounding the signal of the picture image rotated 180° by an affine transformation from the video processor 144 with the signal of the video processor 145; 148 and 149 scopes; 150 a synchronizing signal generator; and 151 a piezoelectric control for controlling the piezoelectric element 132. The synchronizing signal generator 150 is connected to the video processors 143, 144 and 145 and to the piezoelectric control 151. The piezoelectric control 151 is connected to the piezoelectric element 132 and the switchers 146 and 147. The video processors 143, 144 and 145 are connected to the image sensors 126, 125 and 124, respectively, the switcher 146 to the scope 148 and the monitor 139, and the switcher 147 to the scope 149 and the monitor 140.

Figure 15:
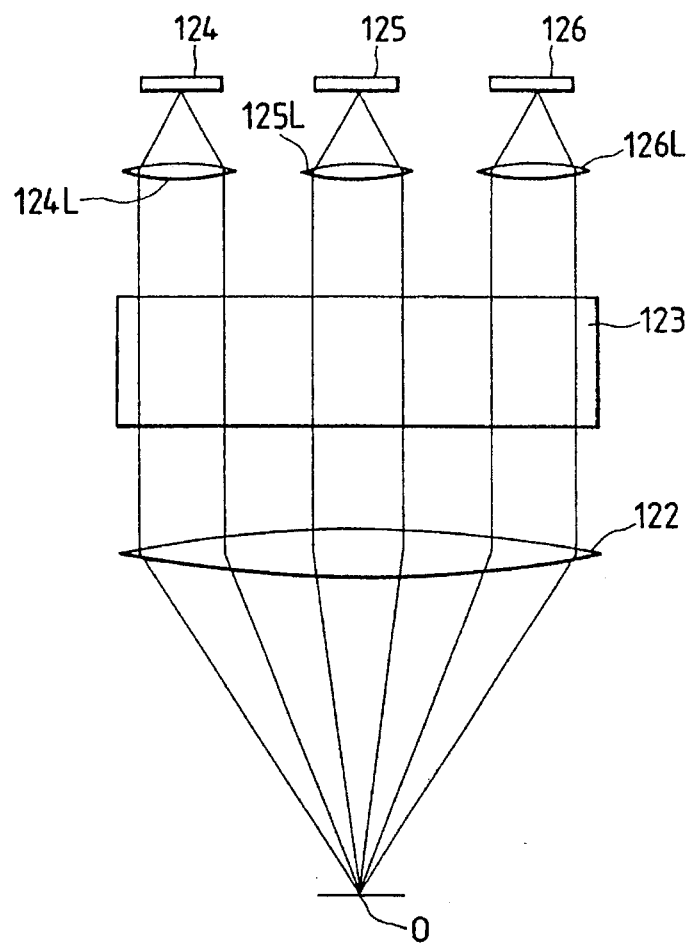
Figure 16:
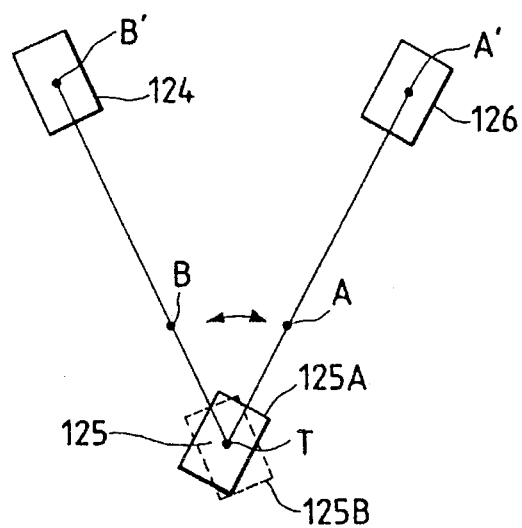

Next, reference is made to the function of the second embodiment. FIG. 15 is a schematic view showing the optical arrangement of the second embodiment and FIG. 16 is an explanatory view showing the orientations of the image sensors 124, 125 and 126. The light from the object O traverses the objective lens 122 and the variable magnification optical system 123 and is imaged at the image sensors 124, 125 and 126 by the imaging lenses 124L, 125L and 126L, respectively. If a negative pulse signal is transmitted from the piezoelectric control 151 to the piezoelectric element 132, the piezoelectric element 132 will be deformed and the driving bar 160 will cause the arm 133 to be moved to the point A of the right end of the guide 131. Since the arm 133 then lies on line T-A' shown in FIG. 8, the image sensor 125 turning together with the arm 133 will follow the same direction as the fixed image sensor 126 (looking from the direction of the arrow $F_A$). In other words, this coincides with the observation direction defined by the monitor 140. When the monitor 139 is set for making observation from the arrow F H direction, the moving arm 129 is moved in accordance with the movement of the monitor 139 as they are united. If the image sensor 124 is located at the point B' in FIG. 16, the image sensors 125 and 126 will follow the directions as indicated by solid lines and the tip of the driving bar 160 will be brought to the point A.

If a positive pulse signal is sent to the piezoelectric element 132 from the piezoelectric control 151, the piezoelectric element 132 will be deformed in the reverse direction mentioned above, as indicated by the broken line in FIG. 8. Consequently, the driving bar 160 causes the arm 133 to be turned to the position B of the stopper 130 of the moving arm 129 in the guide 131. Since the arm 133 stops at the position B, the image sensor 125 follows the same direction as the image sensor 124, as indicated by the broken line in FIG. 16, to coincide with the observation direction defined by the monitor 139.

Figure 17:
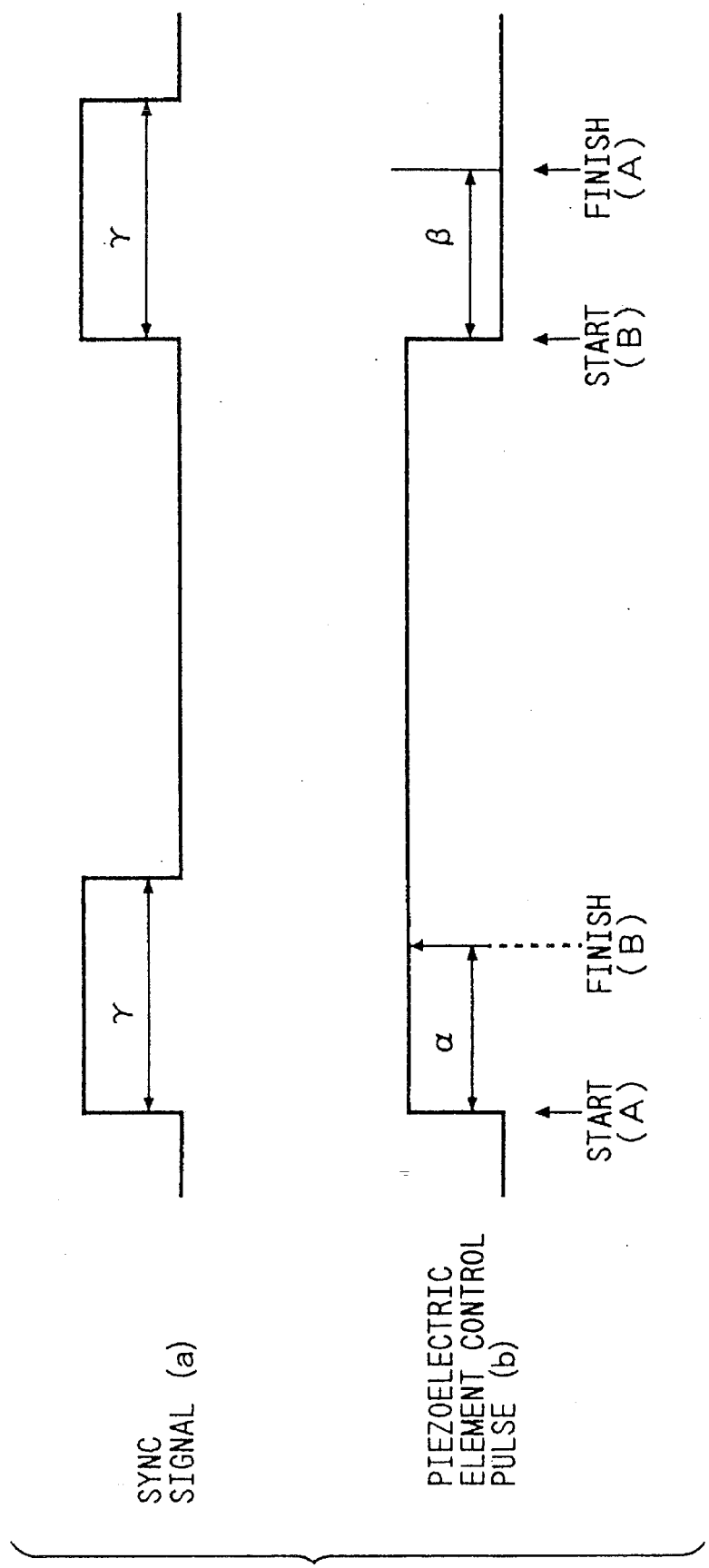

FIG. 17 is a time chart concerning a synchronizing signal (a) transmitted by the synchronizing signal generator 150 and a piezoelectric element control pulse (b) for driving the piezoelectric element 132 by the synchronizing signal (a). The piezoelectric control 151, upon receiving the synchronizing signal (a), applies the positive piezoelectric element control pulse (b) to the piezoelectric element 132. The piezoelectric element 132 is deformed by the pulse (b) and after a time of approximately α, the driving bar 160 is maintained at the point B. When the signal (a) is again inputted to the piezoelectric control 151, the negative piezoelectric element control pulse (b) is applied to the piezoelectric element 132. The piezoelectric element 132 is deformed in the reverse direction and after a time of approximately β, the driving bar 160 arrives at the position of the point A. Thus, by transmitting the sychronizing signal (a) in succession, the image sensor 125 will repeat an oscillating motion between the points A and B, as depicted in FIG. 16.

The signals delivered from the image sensors 124, 125 and 126, after a time of α from the rise of the sychronizing signal (a) and the completion of deformation of the piezoelectric element 132, are transmitted to the video processors 145, 144 and 143, respectively. For the switcher 146, the video signal of the image sensor 126 shown in FIG. 16 is sent from the video processor 143 and that of the image sensor 125 from the video processor 144. As for the switcher 147, the video signal of the image sensor 124 is transmitted from the video processor 145 and that of the image sensor 125 from the video processor 144, so that the video signal of the video processor 144 is turned 180° within the switcher 147 by the affine transformation.

Figure 18:
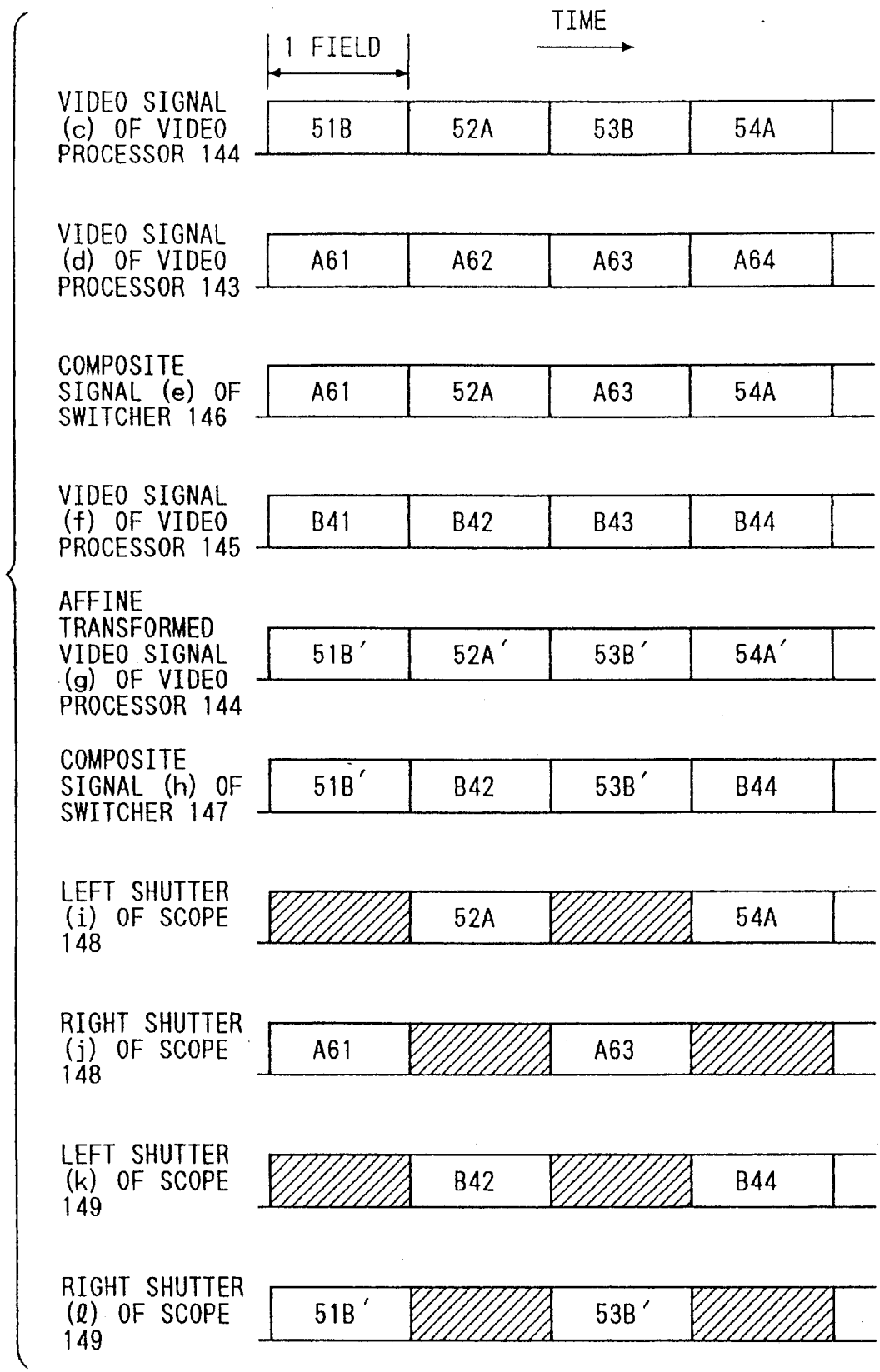

FIG. 18 is an explanatory view showing the input and output signals of the switchers 146 and 147 and the operations of the scopes 148 and 149. Image signals (c) of the video processor 144 are ones at alternate positions 125A and 125B between which the image sensor 125 has been oscillated, as shown in FIG. 16. Reference numerals and symbols 51B and 53B indicate the video signals at the position 125B, and 52A and 54A the video signals at the position 125A. Affine-transformed video signals (g) of the video processor 144 are obtained by turning the video signals (c) of the video processor 144 through 180°, and the signals 51B, 52A, 53B and 54A of the video signals (c) of the video processor 144 correspond to the individuals of the affine-transformed video signals (g) of the video processor 144.

When the piezoelectric control 151 is outputting the pulse signal, the switcher 146 compounds the video signals (c) of the video processor 144 as a composite signal, while if not, it will compound video signals (d) of the video processor 143 to produce composite signals (e) of the switcher 146. The switcher 147, when the control 151 does not output the pulse signal, compounds the affine-transformed video signals (g) of the video processor 144, whereas when outputting the pulse signal, it compounds video signals (f) of the video processor 145 to produce composite signals (h) of the switcher 147. The composite signals (e) of the switcher 146 and the composite signals (h) of the switcher 127 are transmitted to the monitors 139 and 140, respectively, so that the picture images are alternately displayed on both sides. Each of the scopes 148 and 149 for stereoscopic vision connected to the switchers 146 and 147 alternately opens and closes both shutters in synchronization with the alternation of the images of the monitors 139 and 140 (refer to shutters (i), (j), (k) and (l) in FIG. 18). Hence, the stereoscopic picture images can be observed in the direction of $F_A$, shown in FIG. 8, by the monitor 140 and in the direction of $F_B$ by the monitor 139.

If, now, the monitor 139 is turned, the stand 142, the moving arm 129, and the image sensor 124 will be moved to rotate, with their center at the point T, in accordance with the reorientation of the monitor 139. The stopper 130 plugged into the moving arm 129 is also moved within the guide 131. When the positive pulse signal is sent to the piezoelectric element 132, the image sensor 125 is oscillated according to the deformation of the piezoelectric element 132. Since, during the deformation by the positive pulse signal, the piezoelectric element 132 is always maintained at the position of the stopper 130, the image sensors 124 and 125 will take the same direction. Thus, even when the monitor 139 is moved, the picture image displayed on the monitor 139 is always obtained as one looking from the monitor 139.

The second embodiment allows, the equal result to be obtained in a stereomicroscope utilizing a electronic video system which include image sensors and monitors, and reduces the cost since the first and second observers use the image sensor in common.

Figure 19:
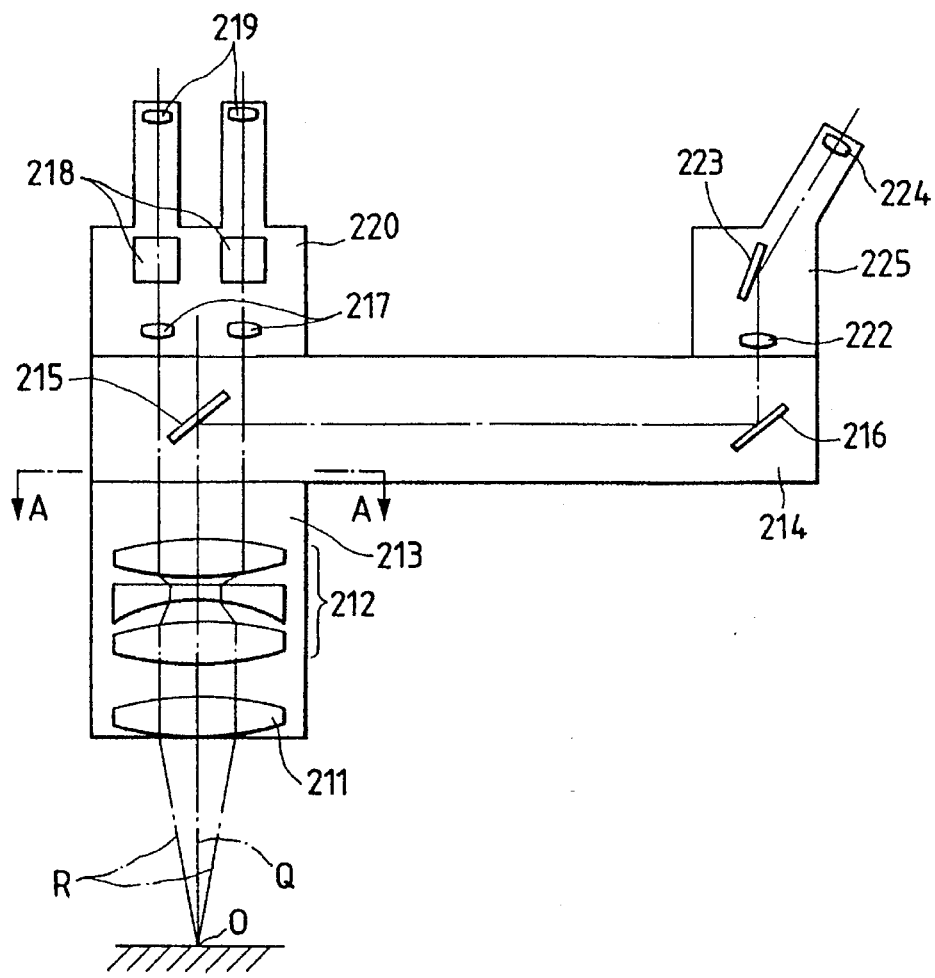
FIGS. 19 to 22 are views showing the optical system of a third embodiment.
Figure 20:
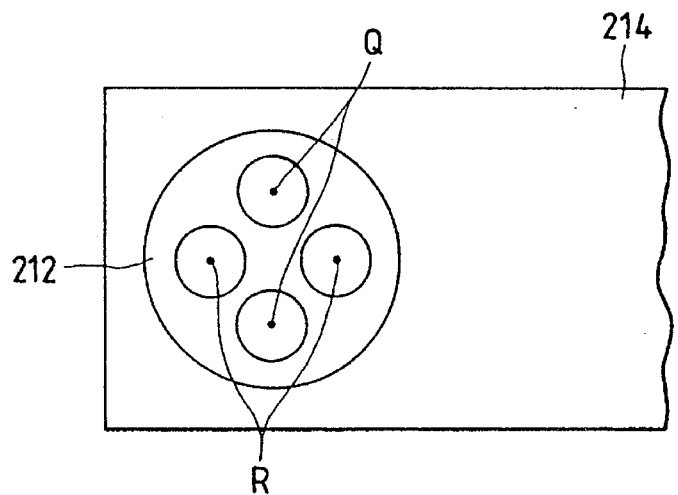
Figure 21:
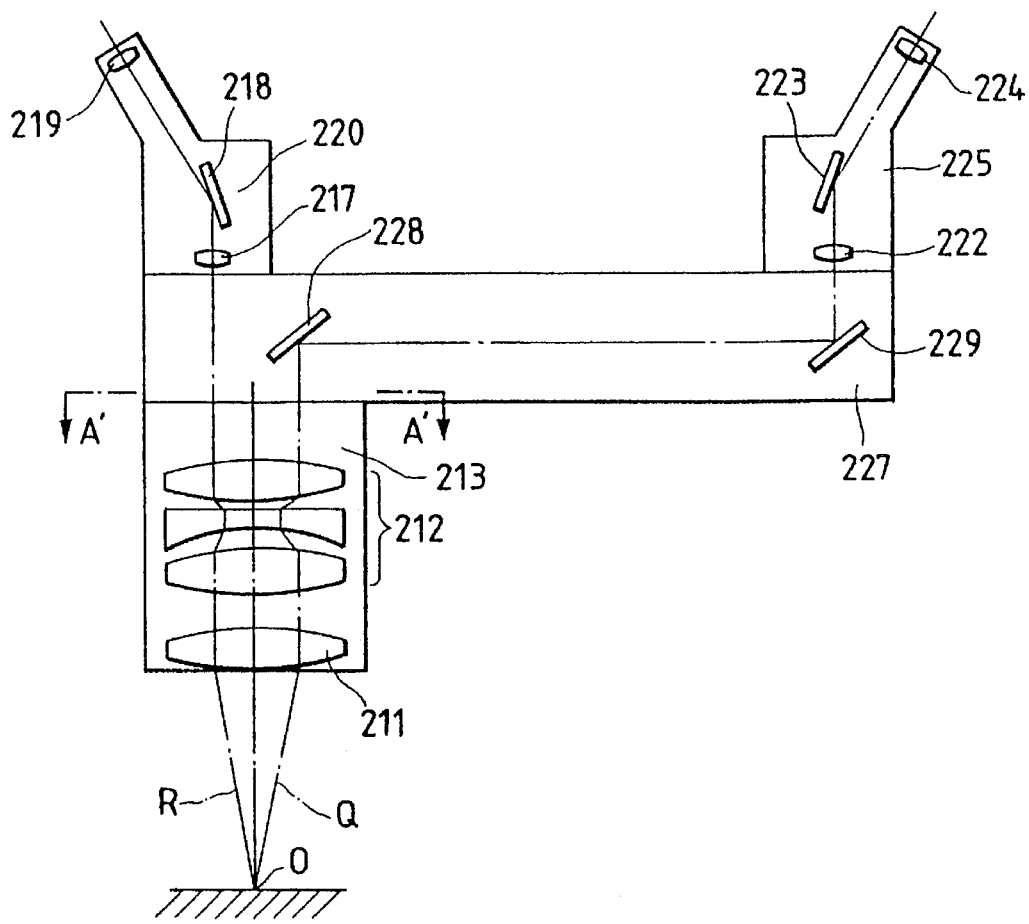
Figure 22:
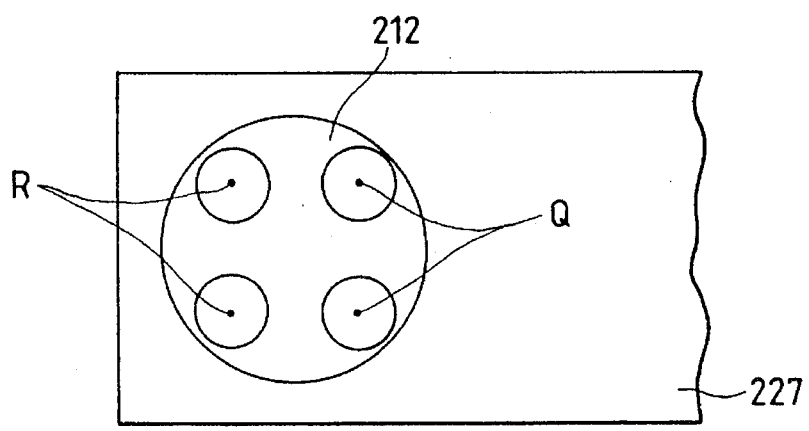

FIGS. 19 to 22 show the third embodiment of the present invention. FIG. 19 is a view showing the optical arrangement of the stereomicroscope; FIG. 20 a sectional view taken along line A—A in FIG. 19; FIG. 21 a view showing the optical arrangement of the stereomicroscope whose intermediate barrel is replaced; and FIG. 22 a sectional view taken along line A'—A' in FIG. 21.

In FIG. 19, reference numeral 211 represents an objective lens located at the lower position of the stereomicroscope; 212 a variable magnification lens system disposed behind the objective lens 211, for making a beam of light passing through the objective lens 211 emergent afocally; and 213 a microscope body in which the objective lens 211 and the variable magnification lens system 212 are incorporated. Reference numeral 214 denotes a first intermediate barrel removably disposed on the microscope body 213, in which numeral 215 designates a pair of first reflecting mirrors aligned in a direction, normal to the plane of the figure behind the variable magnification lens system 212, for deflecting lengthwise the light passing through the variable-magnification lens system 212 within the barrel 214, and 216 a pair of second reflecting mirrors aligned in a direction normal to the plane of the figure, for deflecting the light from the first reflecting mirrors 215 toward the outside of the first intermediate barrel 214. Numeral 217 denotes a pair of first imaging lenses (relay optical system) aligned in a direction parallel to the plane of the figure, , facing against the variable magnification lens system 212 across the first intermediate barrel 214; 218 a pair of third reflecting mirrors located behind the first imaging lenses 217; and 219 a pair of first eyepieces for observing images formed by imaging light reflected from the third reflecting mirrors 218, which are all housed in a first binocular eyepiece barrel 220. The first binocular eyepiece barrel 220 is also removably connected to the first intermediate barrel 214.

Next, in a reflecting optical path from the second reflecting mirrors 216 of the first intermediate barrel 214, reference numeral 222 denotes a pair of second imaging lenses (relay optical system) aligned in a direction normal to the plane of the figure, to image reflected light from the second reflecting mirrors 216; 223 a pair of fourth reflecting mirrors placed behind the second imaging lenses; and 224 a pair of second eyepieces for observing images formed by imaging light reflected from the fourth reflecting mirrors 223, which are all housed in a second binocular eyepiece barrel 225. The second binocular eyepiece barrel 225 is also removably connected to the first intermediate barrel 214.

The first and second binocular eyepiece barrels 220 and 225 are designed so that the optical systems thereof are each provided with an image erecting optical system, not shown. For the light emanating from the object O and passing through the objective lens 211 and the variable magnification lens system 212, reference symbol R is taken as first optical axes of a pair of beams transmitted through the first intermediate barrel 214 and reaching the optical system in the first binocular eyepiece barrel 220, and Q as second optical axes of a pair of beams reflected from the first reflecting mirrors 215 and reaching the optical system in the second binocular eyepiece barrel 225. As seen from the positional relationship between the beams of the optical axes R and Q in regard to the variable magnification lens system 212, illustrated in FIG. 20 which is a cross-sectional view taken along line A—A in FIG. 19, imaginary lines Q—Q and R—R intersect perpendicular to each other.

FIG. 21 is a view of the arrangement of the stereomicroscope in which a second intermediate barrel 227, in place of the first intermediate barrel 214, is removably mounted. In this figure, for the second intermediate barrel 227, reference numeral 228 designates a pair of first reflecting mirrors aligned in a direction normal to the plane of the figure, at the position shifted from the center axis of the variable magnification lens system 212 to the right side of the figure, and 229 a pair of second reflecting mirrors for reflecting the beams deflected by the first reflecting mirrors 228 toward the second binocular eyepiece barrel 225.

Where the second intermediate barrel 227 has been mounted, the first binocular eyepiece barrel 220 is held at the position where it is horizontally rotated 90° from the position indicated in FIG. 19, and the optical system of the first binocular eyepiece barrel 220 is disposed at the position shifted from the center axis of the variable magnification lens system 212 to the left side of the figure so that the beams traveling along the optical axes R are not eclipsed by the first reflecting mirrors 228. As seen from FIG. 22 which is a cross-sectional view taken on line A'—A' in FIG. 21, showing the positional relationship between the beams of the first and second optical axes R and Q in terms of the variable magnification lens system 212, imaginary lines Q—Q and R—R runs parallel to each other.

The third embodiment is constructed as described above, and where the first intermediate barrel 214 has been mounted to the stereomicroscope as shown in FIG. 19, the first binocular eyepiece barrel 220 is arranged so that a pair of optical systems thereof is aligned in a direction perpendicular to the row of the first reflecting mirrors 215. In such an arrangement, the light emitted from the object O traverses the variable magnification lens system 212 through the objective lens 211, thereby being made afocal, and a pair of parallel beams, of the light, including the pair of first optical axes R lying on a plane parallel to the plane of the figure traverses respective sides of the row of the first reflecting mirrors 215 of the first intermediate barrel 214 and enters the first binocular eyepiece barrel 220. Thus, the beams are imaged by the first imaging lenses 217 and reflected from the third reflecting mirrors 218 so that a pair of images of the object O is stereoscopically observed by the first observer through the pair of eyepiece 219.

Of the afocal light passing through the variable magnification lens system 212, on the other hand, a pair of beams including the pair of second optical axes Q lying on a plane normal to the plane of the figure is bent by the pair of first reflecting mirrors 215 of the first intermediate barrel 214 and after being reflected from the pair of second reflecting mirrors 216, enters the second binocular eyepiece barrel 225. Then the beams are imaged by the pair of second imaging lenses 222 and stereoscopically observed, as a pair of images of the object O, through the fourth reflecting mirrors 223 by the second observer through the second eyepieces 224.

Thus, the first and second observers can observe stereoscopically the images of the object O viewed in their respective observation directions with an angle defined therebetween being 90° with the same field and magnification.

Next, in order to alter angle defined between the observers, the second intermediate barrel 227, instead of the first intermediate barrel 214, is attached to the stereomicroscope with the first binocular eyepiece barrel 220 rotated by 90° to connected to the second intermediate barrel 227.

Of the light thus emanating from the object O and made afocally from by the variable magnification lens system 212, the beams including the pair of first optical axes R lying on a plane normal to the plane of the figure are transmitted through the second intermediate barrel 227 and enter the first binocular eyepiece barrel 220. Thus, the images of the object O formed by the first imaging lenses 217 can be stereoscopically observed through the third reflecting mirrors 218 by the first eyepieces 219.

On the other hand, the beams including the pair of second optical axes Q reflected from the first reflecting mirrors 228 of the second intermediate barrel 227 are further reflected by the second reflecting mirrors 229, enter the second binocular eyepiece barrel 225, are imaged by the second imaging lenses 222, and can be stereoscopically observed, as a pair of images, through the fourth reflecting mirrors 223 by the second eyepieces 224.

With such an arrangement, the first and second observers can observe stereoscopically the images of the object O viewed in their respective observation directions, with an angle defined therebetween being 180°.

According to the foregoing embodiment, one of the first and second intermediate barrels 214 and 227 is selected for mounting, thereby enabling the angle between two observers to be set at 90° or 180°. This embodiment, which is simple in structure, small in size, and light in weight, can reduce manufacturing costs. Moreover, since the arrangement has no means for splitting the light subsequent to the variable magnification lens system 212, for example, by half mirrors, individual observation images will be bright. If the number of reflecting mirrors in the intermediate barrels 214 and 227 is properly increased, it is needless to say that the simultaneous observation for three or more persons will be possible. For a plurality of observers, an angle defined between two of the observers can be taken not only at 90° and 180° but at any other angle, as a matter of course.

Figure 23:
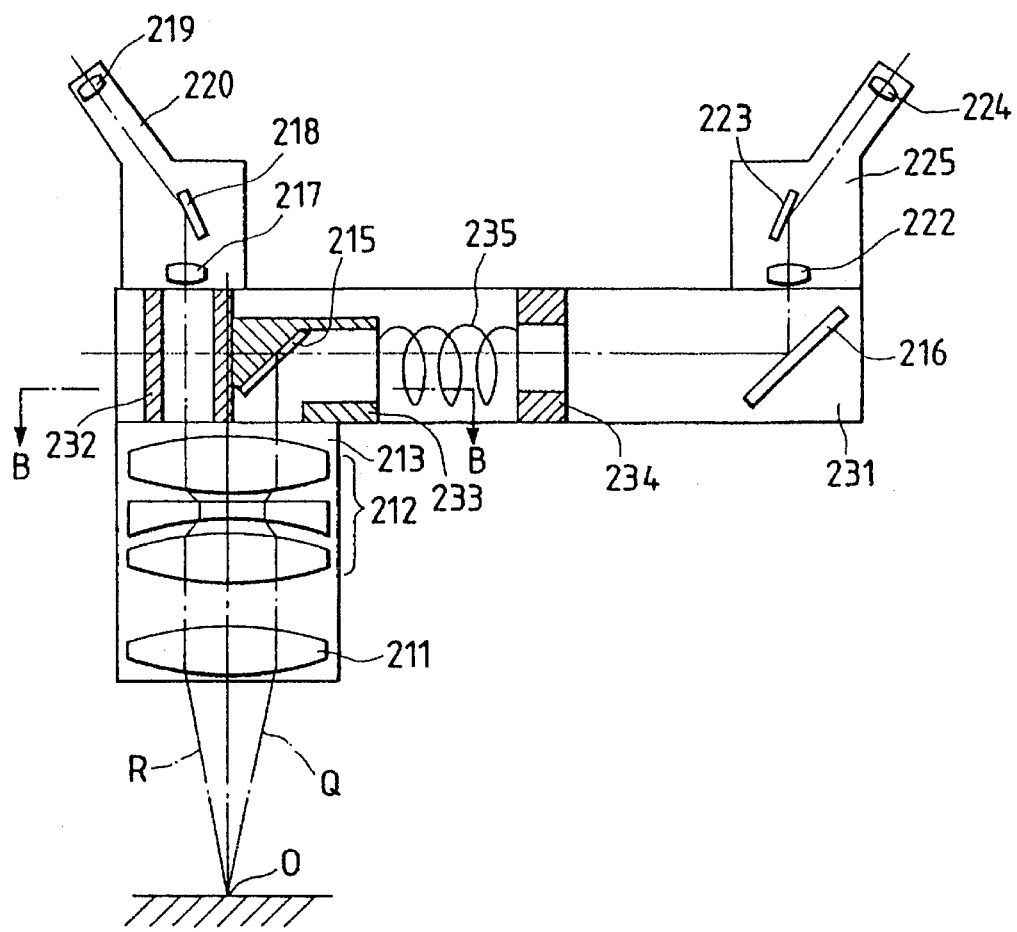
FIGS. 23 to 26 are views showing the optical system and mechanism of a fourth embodiment.
Figure 24:
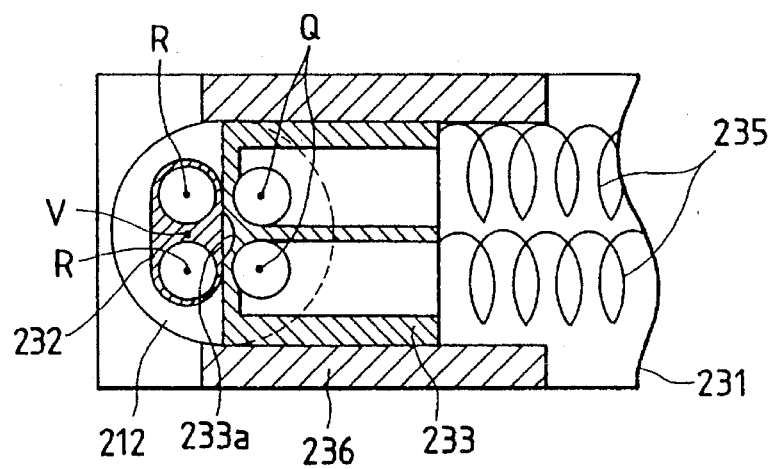
Figure 25:
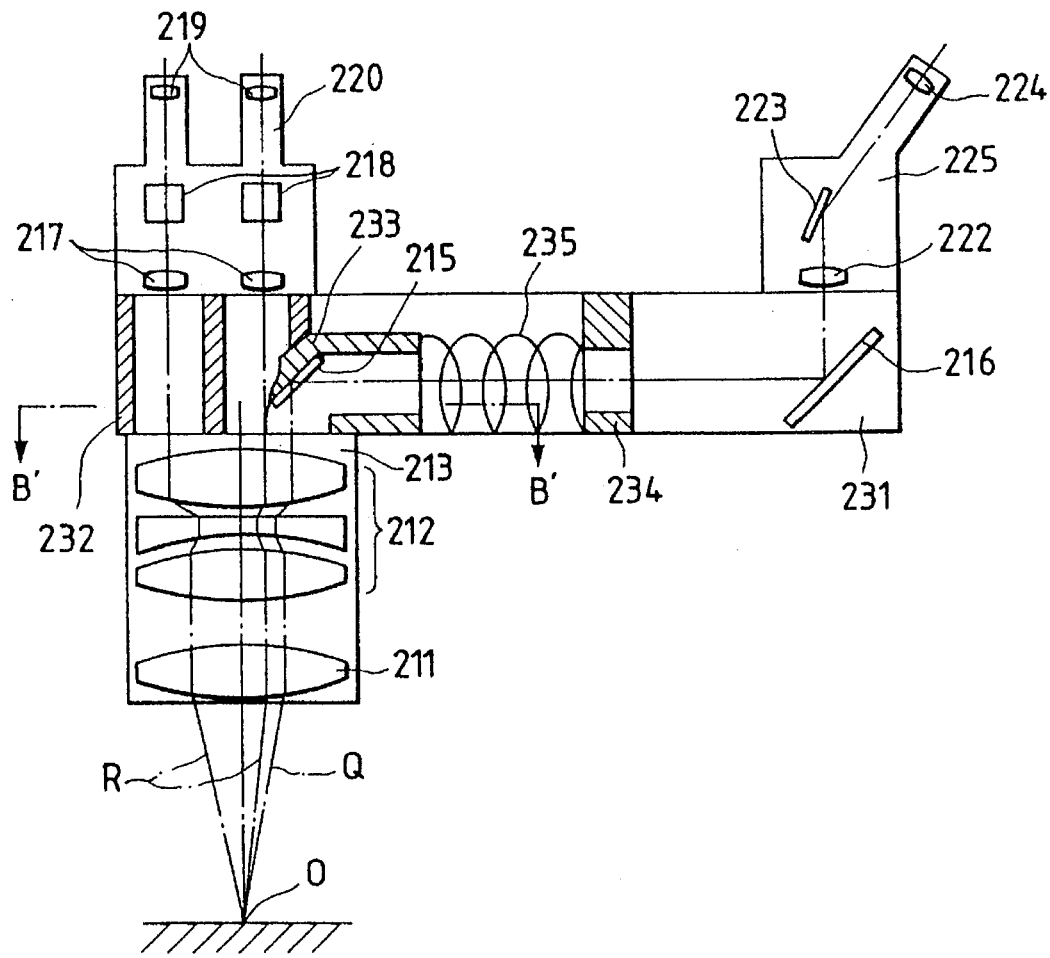

Next, referring to FIGS. 23 to 26, the fourth embodiment of the present invention is explained. FIG. 23 is a view showing a schematic arrangement of the stereomicroscope according to the fourth embodiment; FIG. 24 a sectional view taken along line B—B in FIG. 23; FIG. 25 a view showing a schematic arrangement of the stereomicroscope where the first binocular eyepiece barrel 220 is rotated by 90°; and FIG. 26 a sectional view taken along line B'—B' in FIG. 25.

In FIG. 23, reference numeral 231 represents an intermediate barrel fixedly disposed, in place of the first and second intermediate barrels 214 and 227 of the third embodiment, in which numeral 232 denotes a rotary cylinder of oval cross section (refer to FIG. 24), having a pair of cylinders for transmitting a pair of beams including the first optical axes R for the optical systems housed in the first binocular eyepiece barrel 220, the rotary cylinder being disposed at the position where it is decentered from the center optical axis of the variable magnification lens system 212 to the left side of the plane of the figure and being capable of rotating horizontally (normal to the plane of the figure in FIG. 23), integral with the first binocular eyepiece barrel 220, around an axis V (refer to FIG. 24) located at the intermediate point of the pair of cylinders.

In the intermediate barrel 231, reference numeral 233 denotes a slide cylinder holding a pair of first reflecting mirrors 215, disposed adjacent to the rotary cylinder 232, capable of horizontally sliding, in which the middle of a wall adjacent to the rotary cylinder 232 (between the first reflecting mirrors 215) is formed with an arcuate groove 233a into which a half of the peripheral portion with the oval section of the rotary cylinder 232 can be fitted. Reference numeral 234 represents a wall having a hole for beam transmittion, fixed between the slide cylinder 233 and the second reflecting mirrors 216 in the intermediate barrel 231; 235 a pair of springs interposed between the slide cylinder 233 and the wall 234, for pressing the slide cylinder 233 against the rotary cylinder 232; and 236 an inner wall of the intermediate barrel 231, for guiding the sliding of the slide cylinder 233 within the region thereof (refer to FIG. 24). The second binocular eyepiece barrel 225 is fixed to the intermediate barrel 231.

The fourth embodiment is constructed as mentioned above, so that where a pair of optical axes from the rotary cylinder 232 to the first binocular eyepiece barrel 220 lie on a plane perpendicular to the plane of the FIG. 23 as shown in FIGS. 23 and 24, the slide cylinder 233 is pressed into contact with the rotary cylinder 232 by the springs 235 and hence, the first reflecting mirrors 215 of the intermediate barrel 231 are maintained to be decentered from the center optical axis of the variable magnification lens system 212 to the right side of the plane of the figure. Thus, a part of the light emanating from the object O and emergent afocally from the variable magnification lens system 212 traverses the pair of cylinders of the rotary cylinder 232 in the intermediate barrel 231, as a pair of beams including the pair of first optical axes R, and is imaged by the pair of first imaging lenses 217 so that a pair of images of the object O is stereoscopically observed through the third reflecting mirrors 218 by the pair of first eyepieces 219.

The other part of the light, on the contrary, as a pair of beams including the second optical axes Q reflected from the first reflecting mirrors 215 in the intermediate barrel 231, after being reflected from the second reflecting mirrors 216, is imaged by the pair of second imaging lenses 222 so that a pair of images of the object O is stereoscopically observed through the fourth reflecting mirrors 223 by the second eyepieces 224.

According to the foregoing arrangement, the first and second observers can view stereoscopically the object O in their respective observation directions, with an angle defined therebetween being 180°.

Figure 26:
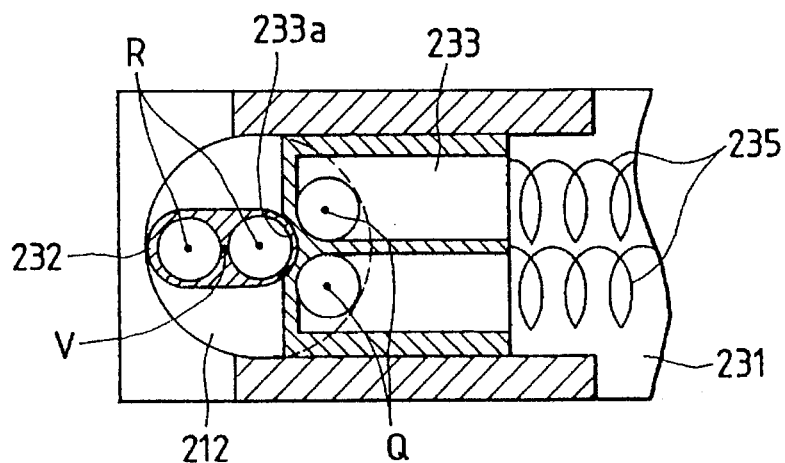

Next, in order to change the observation directions of both observers, when the first binocular eyepiece barrel 220 is horizontally rotated through 90°, the rotary cylinder 232 is also rotated integrally about the axis V. Then, the slide cylinder 233 is moved against the elastic force of the springs 235 toward the second reflecting mirrors 216 and after being moved toward the right along the half of the periphery portion with the oval section of the rotary cylinder 232 turned, is again moved slightly to the left until the groove 233a of the slide cylinder 233 fits the half of the oval periphery portion of the rotary cylinder 232 (refer to FIG. 26). The rotary cylinder 232 and the slide cylinder 233 are thus positioned together with the first binocular eyepiece barrel 220, as shown in FIGS. 25 and 26.

In such an arrangement, of the light emitted from the object O and made afocal through the variable magnification lens system 212 to the beams including the pair of first optical axes R passing through the rotary cylinder 232 of the intermediate barrel 231 are imaged by the pair of first imaging lenses 217 and observed stereoscopically by the pair of first eyepieces 219 wherein each pair of the optical elements being aligned in a direction parallel to the plane of the figure, while the other beams including the pair of second optical axes Q reflected from the pair of first reflecting mirrors 215 in the intermediate barrel 231 are further reflected from the pair of second reflecting mirrors 216, imaged by the pair of second imaging lenses 222, and observed stereoscopically by the pair of second eyepieces 224 wherein each pair of the optical elements being aligned in a direction normal to the plane of the figure.

The first and second observers can thus observe stereoscopically the same object O viewed in their respective observation directions with an angle defined therebetween being 90°.

In the fourth embodiment as described above, where the angle defined between two observers is to be changed from 90° to 180°, and vice versa, the positional adjustment can be done simply by rotating the first binocular eyepiece barrel 220; replacement of intermediate barrels as in the third embodiment is not required.

Figure 27:
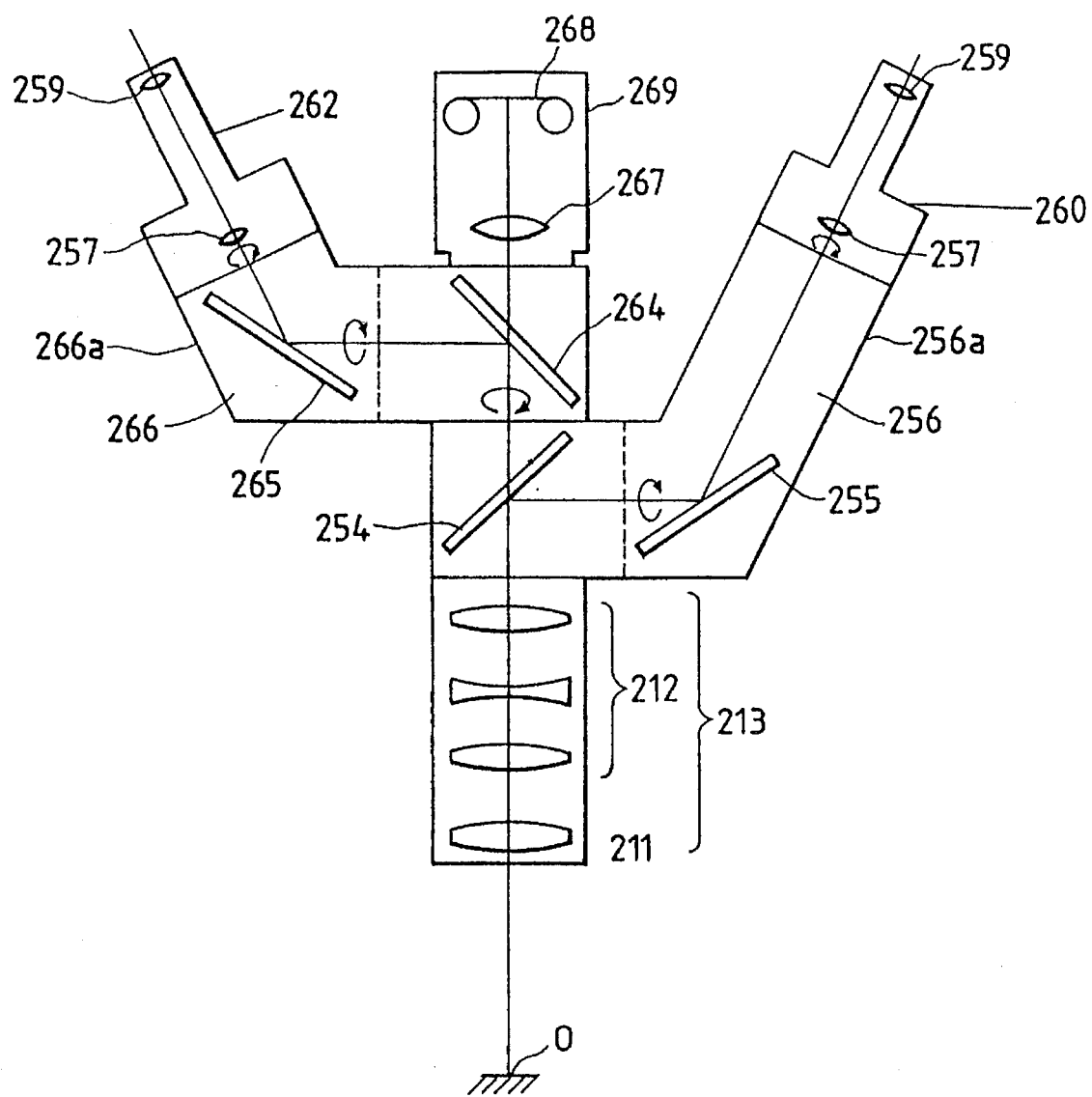
FIGS. 27 to 31 are views showing the optical system and mechanism of a fifth embodiment.

FIG. 27 is a schematic sectional view of the fifth embodiment of the stereomicroscope according to the present invention. Reference numeral 254 designates a first path splitting member and 255 a reflecting member disposed on the path of light reflecting from the first path splitting member 254, which constitute a first housing 256 of the first binocular eyepiece barrel. A portion 256a containing only the reflecting member 255 of the first housing 256 is adapted to be capable of rotating around the optical axis of the path of light reflecting from the first path splitting member 254. Reference numeral 257 represents a pair of imaging lenses (the relay optical system) disposed on the path of light reflecting from the first path splitting member 252 and 259 a pair of eyepieces, which constitute a second housing 260 of the first binocular eyepiece barrel. The second housing 260 is adapted to be capable of rotating around the optical axis of the path of light reflecting from the first path splitting member 254. On the other hand, above the first housing 256, namely, on the path of light passing through the first path splitting member 254, a first housing 266 of the second binocular eyepiece barrel consisting of a second path splitting member 264 and a reflecting member 265 is disposed to be capable of rotating about the optical axis of the path of light passing through the first path splitting member 254. Further, a portion 266a containing only the reflecting member 265 of the first housing 266 is adapted to be capable of rotating about the optical axis of the path of light reflecting from the second path splitting member 264, and a second housing 262 of the second binocular eyepiece barrel consisting of a pair of imaging lenses 257 (the relay optical system) and a pair of eyepieces 259 can be rotated around the optical axis of the path of light reflecting from the reflecting member 265. Additionally, above the first housing 266, that is, on the path of light passing through the second path splitting member 262 is disposed a photographic device 269 incorporating a photographic lens 267 and a recording member 268 such as a film or an image sensor.

The fifth embodiment is designed as mentioned above and hence, the light emanating from the object O passes through the objective lens 211 and the afocal zoom lens 212 and enters the first housing 256 of the first binocular eyepiece barrel. Subsequently, the light reflected from the first path splitting member 254, after being deflected by the reflecting member 255, is observed by the first observer as a stereoscopic image through the pair of imaging lenses 257 and the pair of eyepieces 259 in the second housing 260 of the first binocular eyepiece barrel. On the other hand, the light transmitted through the first path splitting member 254 enters the first housing 266 of the second binocular eyepiece barrel. After the light reflected at the second path splitting member 264 is deflected by the reflecting member 265, it is viewed by the second observer as the stereoscopic image through the pair of imaging lenses 257 and the pair of eyepieces 259 in the second housing 262 of the second binocular eyepiece barrel. Further, the light transmitted through the second path splitting member 264 is imaged on the recording member 268 by the photographic lens 267 and recorded as an image.

Figure 28:
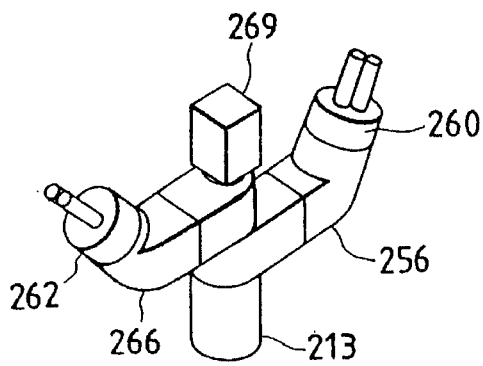
Figure 29:
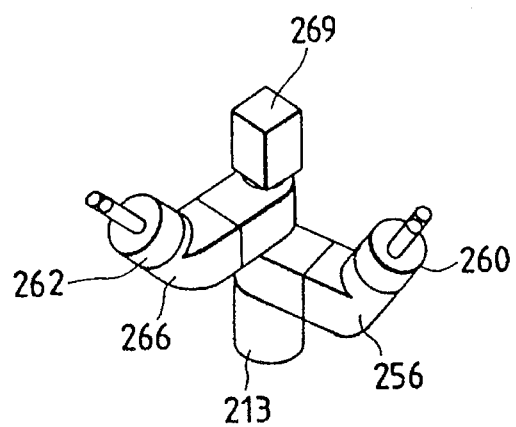
Figure 30:
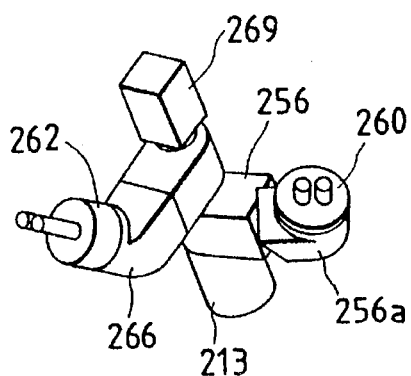

In this embodiment also, the objective lens 211 and the afocal zoom lens system 212 are each single, so that whenever the first and second housings 256, 266, 260 and 262 of the first and second binocular eyepiece barrels are turned, the images are not eclipsed. In the embodiment, which is provided with many rotatable parts, the first and second observers can observe stereoscopically the same object O in the same situation and in their easy postures at any positions, according to operating manners, as shown in FIGS. 28 to 30, in any case where they face each other (FIG. 28), they follow the directions perpendicular to each other (FIG. 29), and the entire microscope is inclined and the portion 256a of the path splitting section is rotated. In the case of FIG. 30, it is also effective that in addition to the above arrangement of the embodiment, a known image rotation optical system (image rotator) is disposed for correcting the rotation of the image on the optical path in the first housing 256.

Furthermore, the single construction of the afocal zoom lens system 212 simplifies the mechanism for a lens movement and consequently, dispenses with the need for increases of the size, weight, and cost of the microscopes as a matter of course.

Figure 31:
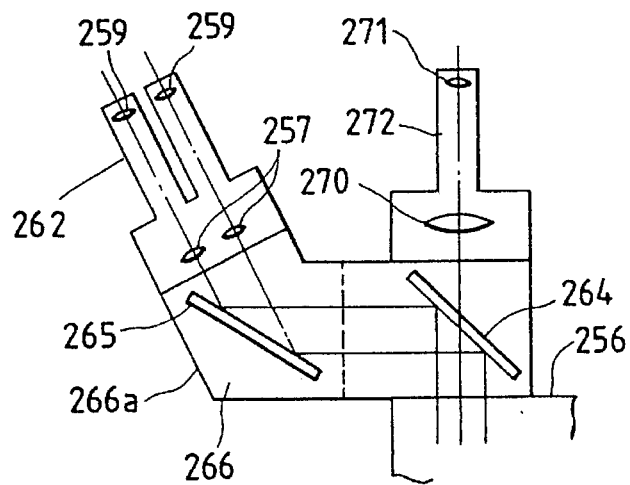

The fifth embodiment has the advantages that because the second path splitting member 264 is disposed to bend laterally the optical path of the first and second housings 266 and 262 of the second binocular eyepiece barrel, a space provided above the second path splitting member 264 can be effectively utilized and prevents the operations of the first and second observers from being disturbed during the surgical operation, and that because the distances of the object O to both observers can be made equal, the observing conditions of the observers can also be made equivalent. Moreover, according to the embodiment, the photographic lens 267 of the photographic device 269 is not disposed on the optical axis of one of a plurality of variable magnification optical systems as in the prior art, but on the optical path of the single objective lens 211 and the single afocal zoom lens system 212, so that its numerical aperture can be more largely set, which can realize photography with a high-speed shutter using a large amount of light and image recording with high resolution. If, for example, mounted to the microscope is a measuring device instead of the photographic device 269, improvement of accuracy by virtue of the larger numerical aperture is achieved. Further, ifs as shown in FIG. 31, a monocular eyepiece barrel 272 is mounted which houses a single imaging lens 270 and a single eyepiece 271, the imaging lens 270 which is larger in numerical aperture, while providing a monocular vision, still higher an image with high resolution to be observed.

What is claimed is:

1. A stereomicroscope comprising:
  a microscope body which houses,
    a single objective optical system for receiving light from an object to let said light emerge as a first parallel beam, and
    a single afocal variable magnification optical system comprising a plurality of lenses for receiving said first parallel beam from said single objective optical system to let said first parallel beam emerge as a second parallel beam, at least one of said plurality of lenses included in said single afocal variable magnification optical system being movable along an optical axis of said single afocal variable magnification optical system to change spatial intervals between said plurality of lenses for making a change in magnification;
  a plurality of binocular eyepiece barrels each of which houses,
    a pair of imaging optical systems disposed in parallel with each other after said single afocal variable magnification optical system for receiving and imaging a pair of partial beams of said second parallel beam which are separate from each other, on a pair of imaging points, thereby a pair of images being obtained such that parallax is kept therebetween, and
    a pair of eyepiece optical systems disposed after said pair of imaging optical systems for stereoscopic observation; and
  means for moving at least one of said plurality of binocular eyepiece barrels with respect to said microscope body, so that said respective pair of imaging optical systems housed therein moves on a plane perpendicular to said optical axis of said single afocal variable magnification optical system while being kept inserted in said second parallel beam, thereby a pair of partial beams of said second parallel beam to be imaged by said pair of imaging optical systems housed in said binocular eyepiece barrel that is being moved shift within said second parallel beam to be imaged respectively by remaining pairs of imaging optical systems respectively housed in remaining ones of said plurality of binocular eyepiece barrels, while a positional relationship between said pair of partial beams to be imaged by said pair of imaging optical systems housed in said binocular eyepiece barrel that is being moved being kept unchanged.

2. A stereomicroscope according to claim 1, wherein movements of said pair of imaging optical systems housed in said binocular eyepiece barrel that is being moved are made along a circle, with said optical axis of said single afocal variable magnification optical system at a center thereof.

3. A stereomicroscope according to claim 1 or claim 2, further comprising beam splitting means disposed between said microscope body and said binocular eyepiece barrels, for splitting said second parallel beam from said single afocal variable magnification optical system into split beams which are led to respective ones of said binocular eyepiece barrels, wherein said beam splitting means is constructed integral with said binocular eyepiece barrels to be moved with respect to said microscope body.

4. A stereomicroscope according to claim 1 or claim 2, further comprising beam splitting means disposed between said microscope body and said binocular eyepiece barrels, for splitting said second parallel beam from said single afocal variable magnification optical system into split beams which are led to respective ones of said binocular eyepiece barrels, wherein said beam splitting means is constructed integral with said microscope body with respect to which said binocular eyepiece barrels are to be moved.

5. A stereomicroscope according to claim 1 or claim 2, wherein said eyepiece optical systems move integrally with image sensors arranged at the imaging points of said imaging optical systems and include display means for displaying images obtained from said image sensors.

6. A stereomicroscope according to claim 3, wherein said eyepiece optical systems move integrally with image sensors arranged at the imaging points of said imaging optical systems and include display means for displaying images obtained from said image sensors.

7. A stereomicroscope according to claim 4, wherein said eyepiece optical systems move integrally with image sensors arranged at the imaging points of said imaging optical systems and include display means for displaying images obtained from said image sensors.

* * * * *